(12) United States Patent
Itoi

(10) Patent No.: US 6,932,781 B2
(45) Date of Patent: Aug. 23, 2005

(54) SHOULDER DISLOCATION ACUTE-PHASE IMMOBILIZATION ORTHOSIS

(75) Inventor: Eiji Itoi, Akita (JP)

(73) Assignee: A.T. Labo, Co., LTD, Akita (JP)

(*) Notice: Subject to any disclaimer, the term of this patent is extended or adjusted under 35 U.S.C. 154(b) by 58 days.

(21) Appl. No.: 10/618,040

(22) Filed: Jul. 11, 2003

(65) Prior Publication Data

US 2004/0129278 A1 Jul. 8, 2004

(30) Foreign Application Priority Data

Jan. 8, 2003 (JP) ......................................... 2003-002463
Mar. 13, 2003 (JP) ......................................... 2003-068426

(51) Int. Cl.⁷ ................................................. A61F 5/00
(52) U.S. Cl. ............................... 602/20; 602/5; 602/21; 602/22; 128/869; 128/878
(58) Field of Search ........................... 602/4–5, 20–22, 602/62; 128/869, 874, 878, 881; 2/459–462, 16, 44–45

(56) References Cited

U.S. PATENT DOCUMENTS

| | | | | |
|---|---|---|---|---|
| 4,375,809 A | * | 3/1983 | Meals ........................... | 602/13 |
| 4,576,351 A | * | 3/1986 | Brink ........................... | 248/118 |
| 4,598,701 A | * | 7/1986 | Schaefer ........................ | 602/19 |
| 4,836,195 A | * | 6/1989 | Berrehail ....................... | 602/20 |
| 4,896,660 A | * | 1/1990 | Scott ............................ | 602/20 |
| 4,986,266 A | | 1/1991 | Lindemann | |
| 5,167,598 A | * | 12/1992 | Sands ........................... | 482/74 |
| 5,329,941 A | * | 7/1994 | Bodine, Jr. ................... | 128/845 |
| 5,423,333 A | * | 6/1995 | Jensen et al. ................. | 128/878 |
| 5,665,058 A | * | 9/1997 | Young ........................... | 602/20 |
| D396,261 S | * | 7/1998 | Duncan ....................... | D22/126 |
| 6,126,622 A | * | 10/2000 | Darcey et al. ................. | 602/5 |
| 6,132,393 A | | 10/2000 | Lundberg | |
| 2005/0010147 A1 | * | 1/2005 | Kazmierczak et al. ......... | 602/4 |

FOREIGN PATENT DOCUMENTS

| | | | | |
|---|---|---|---|---|
| DE | 3517343 | * | 11/1986 | ............. A61F/5/04 |
| DE | 4134969 | * | 4/1993 | ............. A61F/5/04 |
| EP | 362528 | * | 8/1989 | ............. A61F/5/37 |
| FR | 2619307 | * | 8/1987 | ............. A61F/5/02 |
| JP | 2001-299789 | * | 10/2001 | ............. A61F/5/01 |

* cited by examiner

Primary Examiner—Henry Bennett
Assistant Examiner—Amanda Wieker
(74) Attorney, Agent, or Firm—Intellectual Property Law Group LLP; Otto O. Lee; Jurreko Jackson

(57) ABSTRACT

The present invention is a shoulder dislocation acute-phase immobilization orthosis for supporting, in treatment for a shoulder dislocation, an arm in a prescribed position while the elbow is bent at a right angle in an arm hanging position. The orthosis comprises: a support frame (1) integrally formed of a lightweight hard thick-plated material, with a width approximately greater than that of the forearm, comprising: a curved portion (3) which follows the shape of the abdominal part of a body and an arm supporting side face (5) of approximately the forearm length, which is integrally extended forward from one end of the curved portion (3) via a bent portion (4) and is bent at an appointed angle; an arm supporting member(s) (6) for immobilizing the forearm, provided on the arm supporting side face (5) of the support frame (1); and a wrap-around belt (2) made of a flexible material having a width identical to that of the support frame 1, provided with a surface fastener (8) for fitting the support frame (1) to the trunk part of a body.

2 Claims, 5 Drawing Sheets

SHOULDER DISLOCATION ACUTE-PHASE IMMOBILIZATION ORTHOSIS

BACKGROUND OF THE INVENTION

1. Technical Field of the Invention

The present invention relates to a shoulder dislocation acute-phase immobilization orthosis for immobilizing the shoulder joint in a prescribed position.

2. Prior Art

Treatment of a shoulder dislocation has been carried out by supporting the arm immobilized in a sling suspended from the neck.

However, when the arm is suspended by the use of the sling suspended from the neck, the shoulder is immobilized in an internally rotated position.

However, recent studies have revealed that an internally rotated position was not favorable and an externally rotated position was favorable.

In addition, it has been far from being easy to suspend the arm in a sling, and in some cases, the arm weight onto the neck or shoulders causes discomfort or even pain for the patient.

Therefore, a lightweight shoulder dislocation immobilization orthosis, which can respond to various limb positions and can also easily respond to individual patients and can provide sufficient immobilization despite patient's movement, has been widely known as in Japanese Unexamined Patent Publication No. 2001-299789.

According to Japanese Unexamined Patent Publication No. 2001-299789, as shown in FIGS. 8a and 8b, either the E or F-surface of an immobilizer 1 is placed on the abdominal part and the other surface is placed in contact with a patient's forearm part, and the upper limb of the affected side is retained and immobilized by two upper-limb holding belts 10, and while a suspender belt 13 whose length has been adjusted is placed on the unaffected-side shoulder, the same is led behind and is fixed to the immobilizer 1.

Furthermore, as shown in FIGS. 8c and 8d, in order to improve stability of immobilizer 1, one end 17 on an undivided side of a fixture holding belt 16 is fixed onto a surface D of the immobilizer 1, one of the other divided ends 18 is fixed to a surface A, the other thereof is fixed to a surface F, whereby the fixture holding belt 16 is coupled to the immobilizer 1 in a manner covering the abdominal part and waist part.

The respective belts 10, 13, and 16 and the immobilizer 1 are fixed to each other via surface fasteners.

SUMMARY OF THE INVENTION

It is an object of the present invention to provide a shoulder dislocation acute-phase immobilization orthosis which supports, in treatment for a shoulder dislocation, the shoulder in a prescribed position while the elbow is bent at a right angle in an arm hanging position.

Therefore, a shoulder dislocation acute-phase immobilization orthosis of an embodiment of the present invention comprises: a support frame integrally formed of a lightweight hard thick-plated material, with a width approximately greater than that of the forearm, comprising: a curved portion which follows the shape of the abdominal part of a body and an arm supporting side face of approximately the forearm length, which is integrally extended forward from one end of the curved portion via a bent portion and is bent at an appointed angle; and a wrap-around belt made of a flexible material having a width identical to that of the support frame, provided with a surface fastener for fitting the support frame to the trunk part of a body.

In addition, the bent portion can be plastically deformed by a bending force of both arms or more, and can change the angle of inclination of the arm support side face within a prescribed angle range of −20°~30°.

In addition, the arm-supporting member can be detachably fixed to the arm supporting side face.

Furthermore, a shoulder dislocation acute-phase immobilization orthosis of another embodiment of the present invention comprises a roughly triangular support block formed of a lightweight hard synthetic resin material, with a width approximately greater than that of the forearm, comprising: a curved portion which follows the shape of the abdominal part of a body; an arm supporting side face of approximately the forearm length, which is extended forward from both ends of the curved portion to create an angle of inclination within a range of 5°~10° outward from at least one flank side of the user; and an inclined front face provided with an arm supporting member for immobilizing the forearm on the arm supporting side face, mated to said arm supporting side face from the other flank side of the user; and a wrap-around belt made of a flexible material having a width identical to that of the support block, provided with a surface fastener for fitting the support block to the trunk part of a body. The arm supporting member can also be detachably fixed to the arm supporting side face via a surface fastener.

As such, a shoulder dislocation acute-phase immobilization orthosis of the embodiment of the present invention can, in treatment for a shoulder dislocation, allow the angle of the upper arm to be changed within a horizontal angle range of −20°~30° and the arm to be immobilized while the elbow is bent at a right angle in an arm hanging position, therefore, a shoulder dislocation can be reliably healed.

In addition, since no suspension from the neck is required, no arm weight is given to the neck or shoulders, causing no distress or pain.

DETAILED DESCRIPTION OF SPECIFIC EMBODIMENTS

Hereinafter, an embodiment of the present invention will be described based on the attached drawings.

Figure 1:
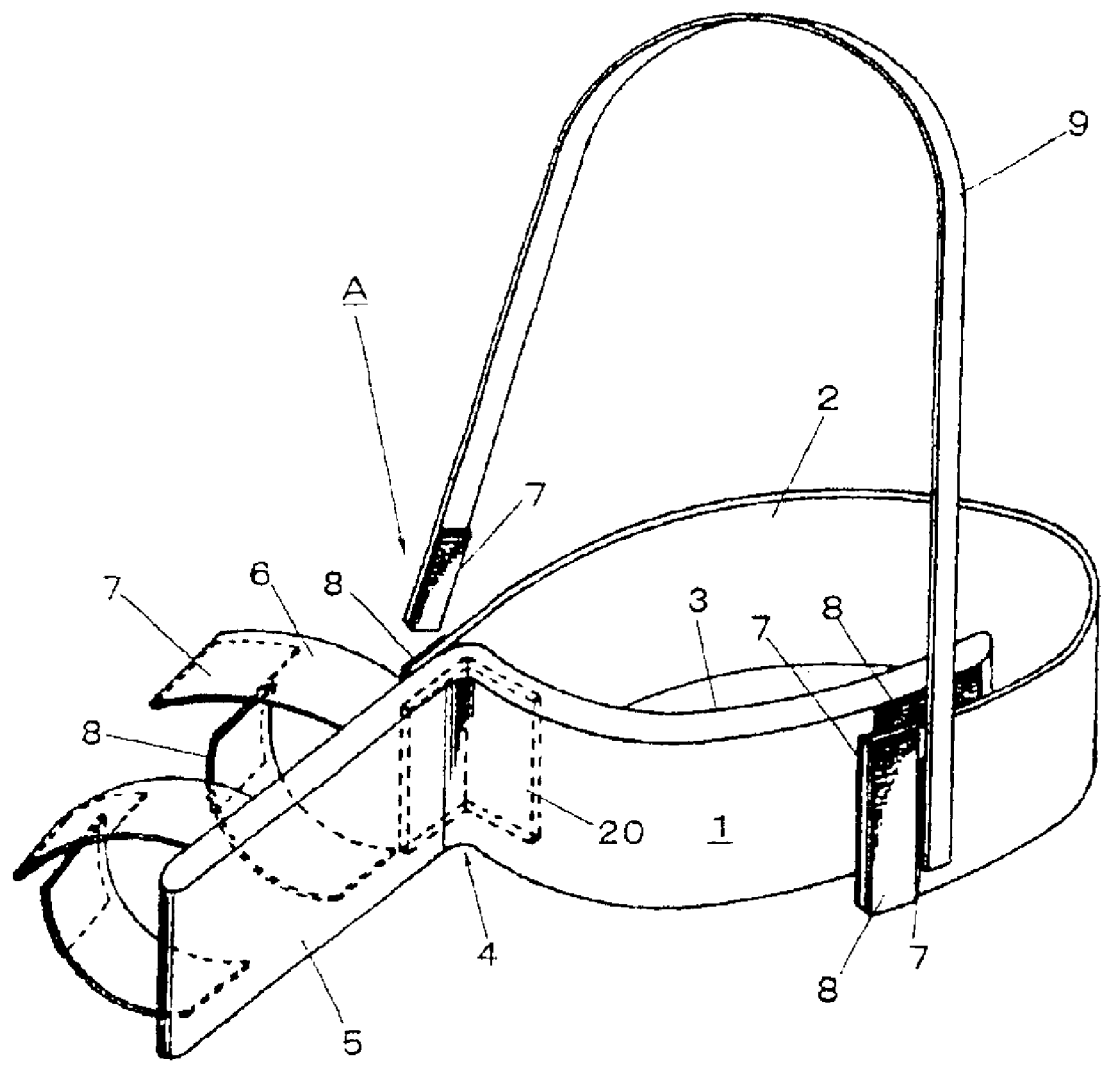
FIG. 1 is a perspective view of a shoulder dislocation acute-phase immobilization orthosis A of an embodiment of the present invention.

A shoulder dislocation acute-phase immobilization orthosis A of an embodiment of the present invention comprises, as shown in FIG. 1, a support frame 1 formed by bending a thick plate of an appointed length and a wrap-around belt 2 for fitting and fixing the support frame 1 around the trunk part of a body.

The support frame 1 is integrally formed of a lightweight hard thick-plated material made of, for example, wood or a synthetic resin such as polyethylene, polypropylene, or styrene foam, with a width greater than that of the forearm, and comprises: a curved portion 3 which follows the shape of the abdominal part of a body; and an arm supporting side face 5 of approximately the forearm length, which is integrally extended forward from one end of the curved portion 3 via a bent portion 4 and is bent at an appointed angle.

For example, if the support frame 1 is made of a synthetic resin, the bent portion 4 is formed with a thin thickness to become a hinge mechanism, and a bent plate 20 such as an aluminum metal plate whose section has a dogleg shape is embedded in the bent portion 4 so that a plastic deformation is possible by a bending force of both arms or more.

Herein, the bent plate 20 also serves as a reinforcement of the bent portion 4.

The bent portion 4 can change the arm supporting side face 5 in its angle within a prescribed angle range of −20°~30°, and an optimal angle is within a range of 5°~10°.

Figure 7:
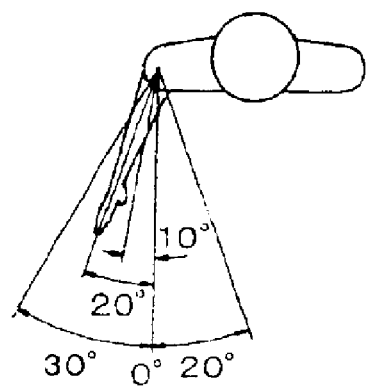
FIG. 7 is a plan view for explaining a horizontal angle of the arm of an embodiment of the present invention.
Figure 8:
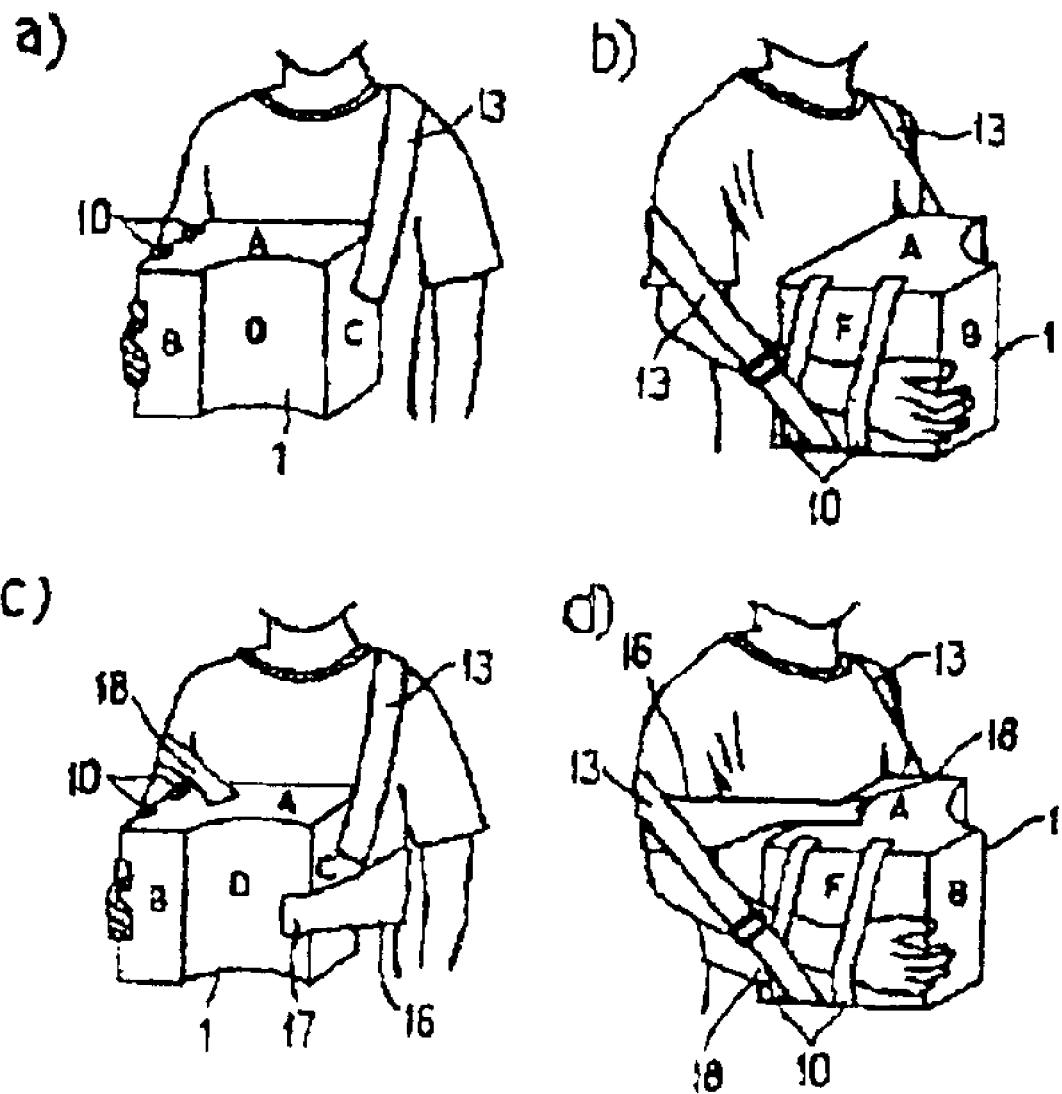
FIGS. 8a–8d are perspective views of a conventional shoulder joint immobilization orthosis in a usage condition.

As shown in FIG. 7, 0° is an angle in a neutral position where the arm is, in a full-face pose, extended forward in parallel with the flank side of the user, −20° is an angle in an internally rotated position where the arm is rotated from the 0° position in a direction to approach the abdominal part, and 30° is an angle in an externally rotated position where the arm is rotated from the 0° position in a direction to become distant from the abdominal part.

In addition, to the outside of the arm supporting side face 5 of the support frame 1, an arm supporting member 6 of a wide-width band is adhered and fixed via its rear surface in the up-and-down direction, and a male (hook) surface fastener 7 is provided on the inside of one end of the arm supporting member 6, and a female (loop) surface fastener 8 is provided on the outside of the other end of the arm supporting member 6.

Herein, although two arm supporting members 6 were formed on the front and back in FIG. 1, one wide-width band fully across the length of the arm supporting side face 5 may be employed. In addition, arm supporting member 6 can also be detachably fixed to the arm supporting side face 5 via a surface fastener.

The wrap-around belt 2 is made of a flexible belt-like material made of leather, cloth, synthetic fiber, or synthetic resin having a width identical to that of the support frame 1, one end thereof is fixed to the bent portion 4 side of the support frame 1, and the other end is provided as a free end, whose inner surface is provided with a male (hook) surface fastener 7.

Herein, the male (hook) surface fastener 7 of the wrap-around belt 2 is engaged with the female (loop) surface fastener 8 attached to the surface of the curved portion 3 of the support frame 1.

On the outer surface of the wrap-around belt 2 of the bent portion 4, provided is a female (loop) surface fastener 8, and on the outer surface of the other end of the wrap-around belt 2, provided is a female (loop) surface fastener 8.

And, for suspension from the neck, a suspension band 9 having, on the inside of both ends, male (hook) surface fasteners 7, is provided, and by respectively engaging the male (hook) surface fasteners 7 of the suspension band 9 with the female (loop) surface fastener 8 on the outer surface of the wrap-around belt 2 of the bent portion 4 and the female (loop) surface fastener 8 on the outer surface of the other end of the wrap-around belt 2, the arm can be suspended.

Next, another embodiment of the present invention will be described based on the attached drawings.

Unlike the above-described shoulder dislocation acute-phase immobilization orthosis A, in which the angle of the arm supporting side face 5 can be changed, in a shoulder dislocation acute-phase immobilization orthosis B of another embodiment of the present invention, an arm supporting side face 5 is fixed to an angle within a horizontal angle range of 5°~10° in an externally rotated position.

Herein, although the design of the horizontal angle can be changed within a prescribed angle range of −20°~30° as in the above-described shoulder dislocation acute-phase immobilization orthosis A, an optimal angle is within a range of 5°~10°.

Figure 2:
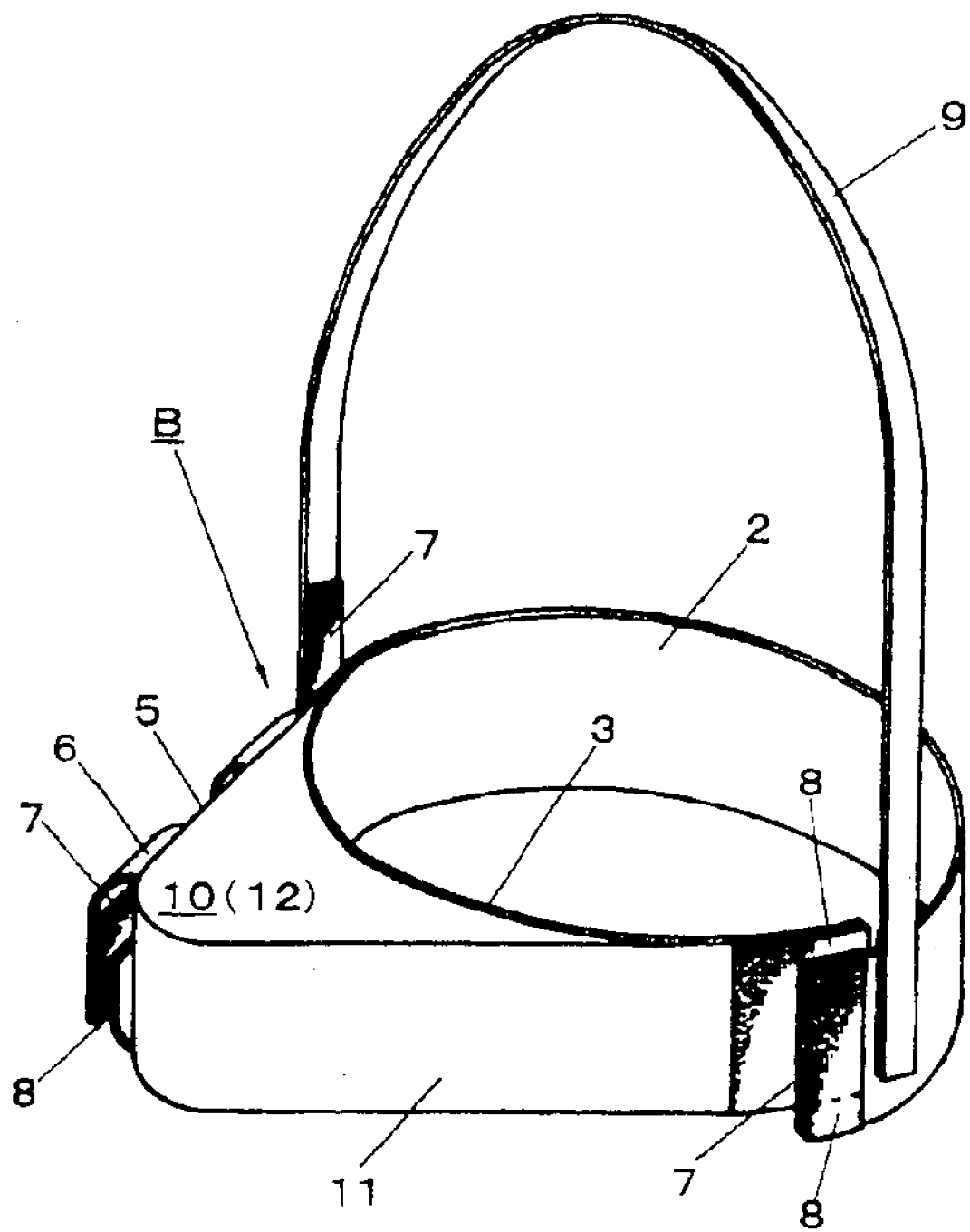
FIG. 2 is a perspective view of a shoulder dislocation acute-phase immobilization orthosis B of an embodiment of the present invention.

The shoulder dislocation acute-phase immobilization orthosis B embodiment of the present invention comprises, as shown in FIG. 2, a roughly triangular support block 10 of an appointed thickness and a wrap-around belt 2 for fitting and fixing the support block 10 around the trunk part of a body.

The support block 10 is formed of a lightweight hard synthetic resin material made of, for example, polyethylene, polypropylene, or styrene foam, with a width greater than that of the forearm, and has a roughly triangular shape comprising: a curved portion 3 which follows the shape of the abdominal part of a body; an arm supporting side face 5 of approximately the forearm length, which is extended forward from one end of the curved portion 3 to create an angle within a range of 5°~10° outward from one flank side of the user; and an inclined front face 11 mated to the supporting side face 5 from the other flank side of the user.

In addition to the arm supporting side face 5 of the support block 10, an arm supporting member 6 of a belt-like band is adhered and fixed via its rear surface in the up-and-down direction, and surface fasteners 7 and 8 are respectively provided on the front ends of the same. Arm supporting member 6 can also be detachably fixed to the arm supporting side face 5 via a surface fastener 8.

The wrap-around belt 2 is made of a flexible material made of leather, cloth, synthetic fiber, or synthetic resin having a width identical to that of the support block 10, one end thereof is fixed to the arm supporting side face 5 side of the support block 10, and the other end is provided as a free end, whose inner surface is provided with a male (hook) surface fastener 7.

Herein, the male (hook) surface fastener 7 of the wrap-around belt 2 is engaged with the female (loop) surface fastener 8 attached to the surface of the inclined front face 11 of the support block 10.

Further, similar to the foregoing, for suspension from the neck, a suspension band 9 having, on the inside of both ends, surface fasteners 7 and 7, is provided. Each surface fastener 7 of the suspension band 9 can be engaged with the surface fastener 8 on the outer surface of the wrap-around belt 2 of the side of the arm supporting side face 5 and the surface fastener 8 on the outer surface of the free end of the wrap-around belt 2, respectively.

Moreover, as a different embodiment, the support block 12 may be formed from a lightweight hard synthetic resin material, for example, a hollow plastic case in a triangular shape.

Next, another embodiment of the arm supporting member 6 to be fixed to the arm supporting side face 5 will be described based on the drawings.

Figure 3:
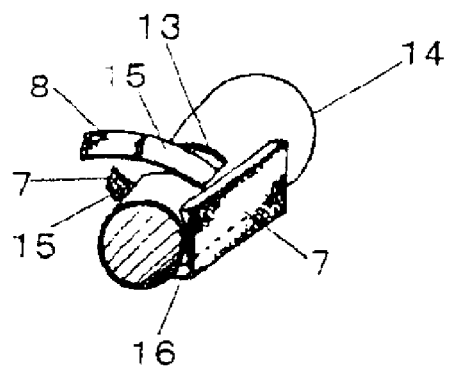
FIG. 3 is a perspective view of a first embodiment of the arm support of the present invention.

As shown in FIG. 3, an arm support member 6 according to the first embodiment comprises a cylindrical arm supporting member 14 formed by forming an opening portion 13 on a part of a cylindrical circumferential surface, a belt-like support band 15 having surface fasteners 7 and 8 on the front ends, and a surface fastener 7 laid on a fixing plate 16 provided on the arm supporting side face 5 of the cylindrical arm supporting member 14.

On the other hand, on the arm supporting side face 5, laid is a surface fastener 8 (female) to be engaged with the surface fastener 7 (male) laid on the fixing plate 16. Arm supporting member 14 can also be detachably fixed to the arm supporting side face 5 via a surface fastener 8.

Accordingly, by inserting an arm into the cylindrical arm supporting member 14 and tightening the support band 15, the arm can be easily supported and immobilized onto the arm supporting side face 5, and in addition, since the cylindrical arm supporting member 14 and fixing plate 16 are joined to the arm supporting side face 5 via the surface fastener 7, the arm can be removed from the arm supporting side face 5 while the same is kept inserted in the cylindrical arm supporting member 14.

Figure 4:
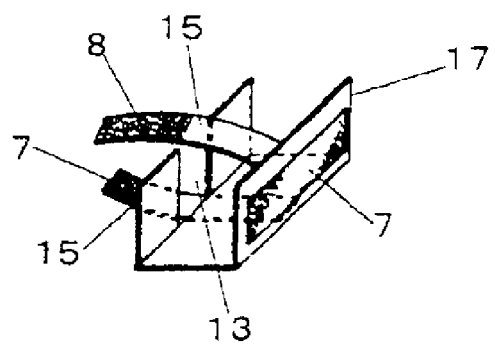
FIG. 4 is a perspective view of a second embodiment of the arm support of the present invention.

As shown in FIG. 4, an arm supporting member 6 according to the second embodiment comprises a gutter-like arm supporting member 17 formed by forming an opening portion 13 on a part of the gutter shape, a belt-like support band 15 formed at the position of the opening portion 13 in a manner sandwiching from the top and bottom, having surface fasteners 7 and 8 on the front ends, and a surface fastener 7 laid on the side of the arm supporting side face 5 of the gutter-like arm supporting member 17.

On the other hand, on the arm supporting side face 5, laid is a surface fastener 8 (female) to be engaged with the surface fastener 7 (male) laid on the arm supporting side face 5 side of the gutter-like arm supporting member 17. Arm supporting member 17 can also be detachably fixed to the arm supporting side face 5 via a surface fastener 8.

Accordingly, by inserting an arm into the gutter-like arm supporting member 17 and tightening the support band 19, the arm can be easily supported and immobilized onto the arm supporting side face 5, and in addition, similar to the aforementioned arm supporting member 14, the arm can be removed from the arm supporting side face 5 while the same is kept inserted in the gutter-like arm supporting member 17.

Figure 5:
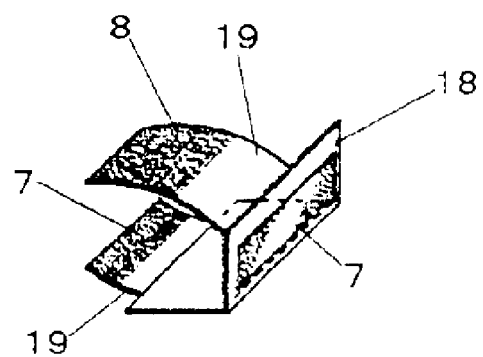
FIG. 5 is a perspective view of a third embodiment of the arm support of the present invention.

As shown in FIG. 5, an arm supporting member 6 according to the third embodiment comprises an arm supporting member 18 formed in an inverted L-shape, a wide-width belt-like support band 19 formed on the inverted L-shaped arm supporting member 18 in a manner sandwiching an arm from the top and bottom, having surface fasteners 7 and 8 on the front ends, and a surface fastener 7 laid on the arm supporting side face 5 side of the inverted L-shaped arm supporting member 18.

On the other hand, on the arm supporting side face 5, laid is a surface fastener 8 (female) to be engaged with the surface fastener 7 (male) laid on the arm supporting side face 5 side of the inverted L-shaped arm supporting member 18. Arm supporting member 18 can also be detachably fixed to the arm supporting side face 5 via a surface fastener 8.

Accordingly, by placing an arm into the inverted L-shaped arm supporting member 18 and tightening the support band 15, the arm can be easily supported and immobilized onto the arm supporting side face 5, and in addition, similar to the aforementioned arm supporting member 14, the arm can be removed from the arm supporting side face 5 while the same is kept inserted in the inverted L-shaped arm supporting member 18.

Next, a case where a shoulder dislocation acute-phase immobilization orthosis A embodiment of the present invention is used will be described based on the drawings.

Figure 6:
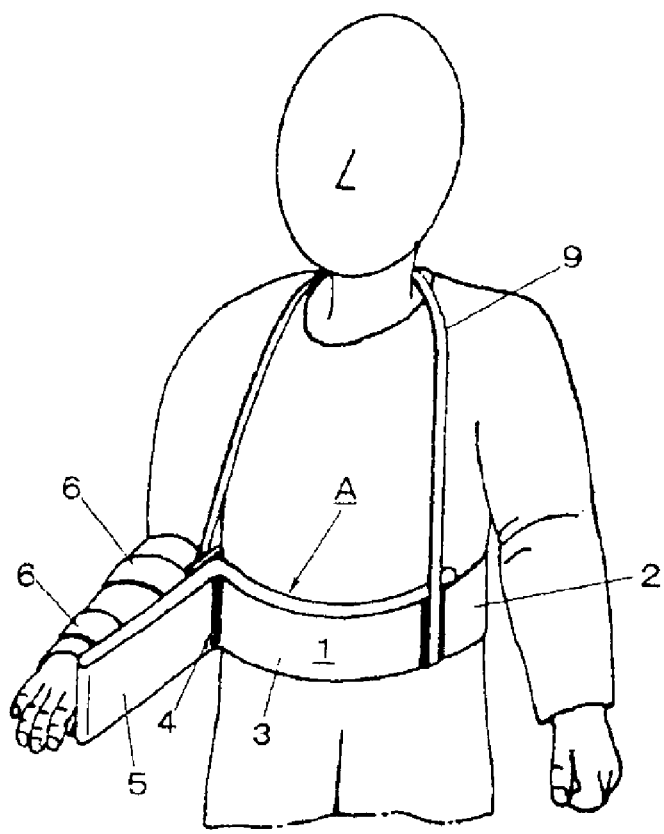
FIG. 6 is an explanatory view of a shoulder dislocation acute-phase immobilization orthosis A of an embodiment of the present invention in a wearing condition.

First, as shown in FIG. 6, the curved portion 3 of the support frame 1 is applied to the abdominal part of a body, the wrap-around belt 2 is led to the back, and by engaging the surface fastener 7 on the free end of the wrap-around belt 2 with the surface fastener 8 on the surface of the curved portion 3, the shoulder dislocation acute-phase immobilization orthosis A is fitted to the trunk part of the body.

Herein, it may also be possible to lead the wrap-around belt 2 to the back after suspending the suspension band 9 from the neck beforehand by engaging the surface fasteners 7 and 7 of the suspension band 9 with the surface fastener 8 on the side of the bent portion 4 of the wrap-around belt 2 and the surface fastener 8 on the free end of the wrap-around belt 2, apply the curved portion 3 of the support frame 1 to the abdominal part of the body, and engage the surface fastener 7 on the free end of the wrap-around belt 2 with the surface fastener 8 on the surface of the curved portion 3, so as to fit the shoulder dislocation acute-phase immobilization orthosis A around the trunk part of the body.

Then, an arm with a splint is applied to the arm supporting side face 5 of the support frame 1, the forearm is wrapped in the arm supporting members 6 from the top and bottom, and the forearm is immobilized by the front-end surface fasteners 7 and 8.

At this time, since the support frame 1 is located at the waist position of the body, the arm is bent at the elbow joint into an L-shape, and as shown in FIG. 6, the forearm is supported and immobilized onto the support frame 1 with an appointed horizontal angle from the flank side of the user.

In addition, in the shoulder dislocation acute-phase immobilization orthosis A, since the bent portion 4 can change the horizontal angle, namely, the angle in the horizontal direction, within a range of −20°~30°, by a preliminary adjustment, the upper arm on the arm supporting side face 5 can be supported at an appropriate position.

As regards the horizontal angle, healing of shoulder dislocation is facilitated as it shifts to the side of external rotation, namely, outside, however, since the forearm is protruded outside from the body, inconvenience occurs in daily life. On the other hand, minimal inconvenience occurs in daily life as it shifts to the side of internal rotation, namely, inside, however, healing of shoulder dislocation is delayed.

Consequently, an optimal range of the horizontal angle is desirably 5°~10° in an externally rotated position. Nevertheless, since the best angle is considered to be different in individual cases, some latitude is allowed for angle adjustment.

Throughout the description and drawings, example embodiments are given with reference to specific configurations. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments of the foregoing description, but rather is indicated by the appended claims. All changes that come within the meaning and range of equivalents within the claims are intended to be considered as being embraced within the spirit and scope of the claims.

What is claimed is:

1. A shoulder dislocation acute-phase immobilization orthosis comprising:

a roughly triangular support block formed of a lightweight hard synthetic resin material, with a width approximately greater than that of a forearm, comprising: a curved portion having two ends which follows the shape of an abdominal part of a body; an arm supporting side face of approximately a forearm length, which is extended forward from one end of the curved portion to create an angle of inclination within a range of 5°~10° outward from at least one of a plurality of flank sides of the user with respect to a surface extended forward in parallel with a flank side of the user; and an inclined front face mated to said arm supporting side face from another flank side of the user;

an arm supporting member for immobilizing the forearm, provided on said arm supporting side face;

a wrap-around belt made of a flexible material having a width identical to that of said support block, provided with a surface fastener on an inner surface of the belt for fitting said support block to a trunk part of the user's body and a plurality of surface fasteners located on an outer surface of the belt, one of the plurality of surface fasteners located on the arm supporting side of the belt, a second of the plurality of surface fasteners located at a free end of the belt; and a suspension band having two ends, provided for suspension around the neck, having a plurality of surface fasteners on an inside of each of the two ends for engaging with the plurality of surface fasteners on the outer surface of the belt, wherein one surface fastener of the suspension band being engaged with the surface fastener of the arm supporting side of the belt and a second surface fastener of the suspension band being engaged with the surface fastener of the free end of the belt.

2. A shoulder dislocation acute-phase immobilization orthosis as set forth in claim 1, wherein said arm supporting member can be detachably fixed to said arm supporting side face via a surface fastener.

* * * * *